United States Patent
Pope et al.

(10) Patent No.: US 6,313,179 B1
(45) Date of Patent: *Nov. 6, 2001

(54) TREATMENT OF HYPERPROLIFERATIVE SKIN DISORDERS WITH C18 TO C20 ALIPHATIC ALCOHOLS

(75) Inventors: Laura E. Pope, Carlsbad; Mohammed H. Khalil; John F. Marcelletti, both of San Diego; Lee R. Katz; David H. Katz, both of La Jolla, all of CA (US)

(73) Assignee: Avanir Pharmaceuticals, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/210,005

(22) Filed: Dec. 11, 1998

Related U.S. Application Data

(63) Continuation of application No. 08/978,213, filed on Nov. 25, 1997, now Pat. No. 5,948,822.
(60) Provisional application No. 60/080,230, filed on Dec. 17, 1996.

(51) Int. Cl.$^7$ .................................................. A61K 31/045
(52) U.S. Cl. ........................................... 514/724; 514/863
(58) Field of Search ...................................... 514/724, 863

(56) References Cited

U.S. PATENT DOCUMENTS

| | | |
|---|---|---|
| 3,592,930 | 7/1971 | Katz et al. . |
| 3,863,633 | 2/1975 | Ryde et al. . |
| 4,186,211 | 1/1980 | Debat . |
| 4,670,471 | 6/1987 | Clark . |
| 4,874,794 | 10/1989 | Katz . |
| 5,070,107 | 12/1991 | Katz . |
| 5,071,879 | 12/1991 | Katz . |
| 5,166,219 | 11/1992 | Katz . |
| 5,194,451 | 3/1993 | Katz . |
| 5,534,554 | 7/1996 | Katz . |

FOREIGN PATENT DOCUMENTS

WO 88/08294    11/1988    (WO) .

OTHER PUBLICATIONS

Berkow, et al., Dermatologic Disorders, The 16 Merck Manual, Merck Research Lab, xp002064741 p. 2460 (1992).
Katz, et al., Antiviral activity of 1–docosanol, an inhibitor . . . , Proc. Natl. Acad. Sci., vol. 88, pp. 108025–10829 (1991).
Pope, et al., Anti–herpes simplex virus activity of n–docosanol correlates with . . . , Journal of Lipid Research, vol. 37, pp. 2167–2178 (1996).
Report of the Centers for Disease Control Task Force on Kaposi's Sarcoma and Opportunistic Infections, Epidemiologic Aspects of the Current Outbreak of Kaposi's Sarcoma . . . , The New England Journal of Medicine, pp. 248–252 (Jan. 28, 1982).
Streitwieser, et al., Introduction to Organic Chemistry (2nd Edition), pp. 160, 243–247, 303–307, 311–312, 315–317, 401–406, 447–453, 516, 660–666, 706 and 670 (1981).

*Primary Examiner*—Rebecca Cook
(74) *Attorney, Agent, or Firm*—Knobbe, Martens, Olson & Bear LLP

(57) ABSTRACT

A method is disclosed for treating a benign or malignant hyperproliferative skin lesion, comprising topically administering a C18 to C20 aliphatic alcohol to the skin lesion in a pharmaceutically acceptable carrier.

7 Claims, No Drawings

TREATMENT OF HYPERPROLIFERATIVE SKIN DISORDERS WITH C18 TO C20 ALIPHATIC ALCOHOLS

RELATED APPLICATIONS

This application is a continuation of Application 08/978,213, filed on Nov. 25, 1997, now U.S. Pat. No. 5,948,822 which claims priority under §119(e) from Provisional Application 60/080,230 filed on Dec. 17,1996.

FIELD OF THE INVENTION

The present invention relates to the treatment of hyperproliferative disorders of the skin by topical administration of a composition comprising one or more C18 to C26 aliphatic alcohols.

BACKGROUND OF THE INVENTION

Benign hyperproliferative disorders of the skin result from excess keratin deposition (hyperkeratosis) of the corneous layer. Such hyperproliferative disorders include epidermolytic hyperkeratosis and follicular keratosis. One common benign hyperproliferative disorder is hypertrophic scar formation (a keloid), a sharply elevated, irregularly-shaped, progressively enlarging scar due to the formation of excessive amounts of collagen in the corium during connective tissue repair following surgical and traumatic lacerations. While such hypertrophic tissue repair is most evident at sites of external wound healing, keloid-prone individuals also manifest hypertrophic scarring internally. The major consequences of external keloid scarring are mainly cosmetic, although keloids can also result in varying degrees of psychological and social trauma for the afflicted individuals. In such cases, surgical or laser intervention is indicated because there is currently no generally effective topical or systemic treatment for this condition. Other hyperproliferative disorders are corns and calluses. Current non-surgical treatments for less acute cases of hyperkeratosis include 17% salicylic acid in collodion and 40% salicylic acid plasters. A keloid is usually treated by injection of a corticosteroid into the base of the lesion. This treatment may flatten the keloid, but is often ineffective.

Malignant hyperproliferative disorders of the skin include Kaposi's sarcoma (KS) and skin cancer. KS is a neoplasm, often associated with AIDS patients, characterized by vascular skin tumors. KS lesions originate from multifocal sites in the mid-dermis and extend to the epidermis. Histopathology shows spindle cells and vascular structures admixed to various degrees. Repeated biopsies show a progressive sarcomatous-like appearance. In more advanced stages, the lesions appear as multiple purplish to brown subcutaneous nodular or plaque-like dermal lesions, often with a varicose surface. The characteristic histological features of KS include the proliferation of spindle-shaped cells (KS cells, considered the tumor element) and of endothelial cells (CDC Task Force on KS and Opportunistic Infections, *New Engl. J. Med.*, 306:248, 1982). There are two types of KS: indolent and lymphadenopathic. Indolent KS is characterized by nodular or plaque-like dermal lesions. Treatment options include freezing, electrocoagulation or electron beam radiotherapy. Unresponsive lesions are treated locally with 1,000–2,000 rads of x-ray therapy.

Aliphatic alcohols are known to have various biological activities. U.S. Pat. No. 3,031,376 discloses that n-tetracosanol (C24), n-hexacosanol (C26), n-octacosanol (C28) and triacontanol (C30) and their esters improved physical performance of athletes and disclosed compositions comprising such alcohols and esters for oral ingestion. U.S. Pat. No. 4,670,471 discloses the use of triacontanol for treatment of inflammatory disorders such as herpes simplex, eczema, shingles, atopic dermatitis and psoriasis. U.S. Pat. No. 3,592,930 discloses a medicant vehicle comprising 15 to 45 parts of saturated aliphatic alcohol having from 16 to 24 carbons as a carrier for antibiotics, steroids and antihistamines. U.S. Pat. No. 3,863,633 discloses a composition for topical treatment of the eye comprising 10–80% C12 to C22 surface active alcohols such as n-docosanol, n-hexadecanol, n-octadecanol and n-eicosanol. U.S. Pat. No. 4,874,794 discloses a method of treating virus-induced and inflammatory diseases of the skin and membranes with a composition comprising one or more of the aliphatic alcohols n-docosanol (C22), n-tetracosanol and n-hexacosanol. Antiviral and anti-inflammatory activities of aliphatic alcohols having from 20 to 32 carbons are disclosed in U.S. Pat. No. 4,874,794, U.S. Pat. No. 5,071,879, U.S. Pat. No. 5,166,219, U.S. Pat. No. 5,194,451 and U.S. Pat. No. 5,534,554. Related chemical compounds and compositions having therapeutic activities are disclosed therein.

A C22 aliphatic alcohol, n-docosanol, suspended in a surfactant exhibits potent antiviral activity against a variety of lipid enveloped viruses including herpes simplex virus and respiratory syncytial virus in cell culture assays (Katz, D. H., et al., *Proc. Natl. Acad. Sci. USA* 88:10825–10829, 1991; U.S. Pat. No. 5,534,554, hereby incorporated by reference). Intracellular metabolic conversions of n-docosanol may account for its antiviral activity (Pope et al., *J. Lipid Res.*, 37:2167–2178, 1996). The alcohol is not cytotoxic in concentrations up to 300 mM.

There is a need for therapeutic agents which will inhibit hyperproliferative skin lesions. The present invention addresses this need.

SUMMARY OF THE INVENTION

One embodiment of the present invention is a method of treating or inhibiting the growth of a hyperproliferative skin lesion in an individual in need thereof, comprising topically administering to the lesion an effective proliferation-inhibiting amount of one or more C18 to C26 aliphatic alcohols in a pharmaceutically acceptable carrier. Preferably, the skin lesion is benign. Advantageously, the said skin lesion is hyperkeratosis or keloid. According to another aspect of this embodiment, the skin lesion is malignant. The skin lesion may be Kaposi's sarcoma or skin cancer. Preferably, the aliphatic alcohol is present in an amount from about 0.1% to 20% by weight; more preferably, the aliphatic alcohol is present in an amount from about 5% to 15% by weight. Advantageously, the aliphatic alcohol is n-docosanol, n-tetracosanol or n-hexacosanol; more advantageously, the aliphatic alcohol is n-docosanol.

DETAILED DESCRIPTION OF THE PREFERRED EMBODIMENTS

The present invention relates to the treatment or growth inhibition of hyperproliferative skin lesions by topical administration of one or more aliphatic straight-chain saturated monohydric alcohols which have from 18–26, preferably 22–26 carbons, in a topically acceptable carrier. Compositions of this invention suitable for use in treating or inhibiting the growth of hyperproliferative skin lesions comprise an active ingredient or combination of compounds as the active ingredient, selected from a group consisting of C18 to C26 saturated aliphatic alcohols and monounsaturated aliphatic alcohols. The C18 to C26 alcohols useful in the present invention include n-eicosanol (C20), n-docosanol (C22), n-tetracosanol (C24) and n-hexacosanol (C26). The use of C22 aliphatic alcohols is particularly preferred. The corresponding low molecular weight ether or ester derivatives of these alcohols (e.g., methyl-, ethyl, propyl-) are also contemplated for use in the present invention.

Methods of synthesis of n-docosanol are known to those skilled in the art (e.g., see U.S. Pat. No. 4,186,211). Methods of synthesis of aliphatic alcohols are well known in the art (e.g., see A. Streitwieser, Jr. & C. H. Heathcock, *Introduction to Organic Chemistry*, 2nd ed., Macmillan Publishing Co., New York, N.Y., 1981, at pages 160, 243–247, 303–307, 311–312, 315–317, 401–406, 447–453, 516, 550–555, 604–605 and 670).

n-Docosanol exhibits antiproliferative activity against cultured hypertrophic fibroblasts. This inhibitory activity is specific to hyperproliferative cell populations, as the growth of normal cells was unaffected under the tissue culture conditions used. Reduction of cell proliferation by n-docosanol is favored by low cell densities and longer incubation times and is concentration-dependent. Unexpectedly, n-docosanol significantly reduced hyperproliferative keloid formation in a patient for whom other treatments had not been successful.

The hyperproliferative skin lesions for treatment with the C18 to C26 aliphatic alcohols may be either benign or malignant. Benign lesions may arise from hyperkeratosis occurring, for example, in keloid, dermatitis papillaris capilliti (acne keloid), fibromatosis gingivae (keloid of gums), epidermolytic hyperkeratosis and follicular keratosis. Malignant lesions include skin cancers (basal cell carcinoma, squamous cell carcinoma, melanoma) and KS. The use of the aliphatic alcohol compositions described herein can be combined with well known treatments for skin cancer (e.g., irradiation and/or chemotherapy) to lead to total or partial remission of the cancerous skin lesion. The treatment of any such hyperproliferative skin lesion is within the scope of the invention.

The active agents and surfactants are combined with a carrier that is physiologically compatible with the skin and membrane tissue of a human or animal to which it is administered. The topically acceptable carrier is non-irritating to the skin and membranes and free from physiological effect.

Suitable carriers include aqueous and oleaginous carriers such as, for example, white petrolatum, isopropyl myristate, lanolin or lanolin alcohols, mineral oil, sorbitan monooleate, propylene glycol, cetylstearyl alcohol (together or in various combinations). The carriers may be combined with a detergent (e.g., polyoxyl stearate or sodium lauryl sulfate) and mixed with water to form a lotion, gel, cream or semi-solid composition. Other suitable carriers comprise mixtures of emulsifiers and emollients with solvents such as sucrose stearate, sucrose cocoate, sucrose distearate, mineral oil, propylene glycol, 2-ethyl-1,3-hexanediol, polyoxypropylene-15-stearyl ether and water. Preservatives may also be included in the carrier including methylparaben, propylparaben, benzyl alcohol and ethylene diamine tetraacetate salts. Preferred carrier formulations are described in U.S. Pat. No. 5,534,554.

Dilute suspensions without thickeners are most suitable for delivery to skin surfaces as aerosol sprays, using well known methods of delivery. The composition may also include a plasticizer such as glycerol or polyethylene glycol (m.w. 800 to 20,000) and penetrants such as azone. The composition of the carrier can be varied so long as it does not interfere with the pharmacological activity of the active ingredients.

The aliphatic alcohol compositions of the invention may additionally employ adjunct components conventionally found in pharmaceutical compositions in their art-established fashion and at their art-established levels. These pharmaceutically active materials do not interfere with the efficacy of the aliphatic alcohols. Thus, for example, the compositions may include anti-microbial agents, anti-viral agents, anti-fungal agents, antioxidants, antipruritics, astringents, local anesthetics, anti-inflammatory agents, buffering agents, sunscreens and cosmetic agents such as coloring agents, fragrances, lubricants, skin penetration enhancers and moisturizers or drying agents. Anti-microbial agents useful for inclusion in the compositions include, for example, polymyxin B and tetracycline. Other anti-viral agents included in the formulations may be nucleoside analogs such as acyclovir or cytokines. Anti-fungal agents that may be included are miconazole or tolnaftate. Antioxidants such as vitamin E may be included. Sunscreens such as para-aminobenzoic acid may be included. Drying agents that may be included are well known, such as, for example, phenol and benzyl alcohol. Lubricants such as synthetic or natural beeswax may also be included. Thickening agents to produce gels or suspensions may include pullulin, xanthan, polyvinylpyrrolidone or carboxymethylcellulose. Other carriers contemplated for use in formulating the aliphatic alcohol compositions include creams, salves, dispersions, suspensions, pastes and ointments. A suitable carrier may include, for example, white petrolatum, stearyl alcohol, isopropyl myristate, sorbitan monooleate, propylene glycol, water and a detergent such as polyoxyl stearate mixed to form a stable cream. The active ingredients (i.e., n-docosanol) comprise about 0.1% to about 50% by weight of the final composition, preferably 1% to 10% by weight. For assistance in formulating the compositions of the present invention, one may refer to *Remington's Pharmaceutical Sciences*, 15th ed., Mack Publishing Co, Easton, Pa., the entire contents of which are hereby incorporated by reference. Exemplary compositions for use in the present invention are disclosed in U.S. Pat. No. 5,534,554.

Another suitable composition for use in the present invention is formulated of stearyl alcohol, petrolatum, water and mineral oil stabilized with a detergent such as sodium lauryl sulfate and may include a preservative such as methylparaben or propylparaben and an effective amount, typically from about 5% to 15% percent by weight of one or more C18 to C26 aliphatic alcohols.

Administration is preferably to the skin or a mucous membrane using a cream, lotion, gel, ointment, suspension, aerosol spray or semi-solid formulation (e.g., a suppository), all formulated using methods well known in the art. Applications of the pharmaceutical compositions containing the active ingredient in an amount between about 0.1% and about 20% (w/w) effective in treating or inhibiting the growth of a hyperproliferative skin lesion consist of about 10 mg to 10 g of the composition per application for between one day and one year. The compositions are typically applied between one and five times per day in an amount sufficient to completely cover the lesion. In a preferred embodiment, one to four applications of the composition per day, of about 0.1 g to 5 g per application, for one to thirty days are sufficient to treat or inhibit the growth of a hyperproliferative skin lesion. The compositions are preferably applied to lesions daily as soon as the lesion is detected and discontinued once the lesion has completely disappeared or exhibits no further reduction in size. Alternatively, the compositions may be used to manage or slow the growth of a lesion such as a tumor. Even when a particular tumor cannot be cured, there is significant value in slowing its rate of growth.

The following study addressed the toxicity and antiproliferative activity of n-docosanol in keloid fibroblasts.

EXAMPLE 1

Antiroliferative Activity of N-docosanol in Keloid Cells

Human keloid fibroblasts were obtained from the American Type Culture Collection (Rockville, Md.) (CRL 1762). n-Docosanol (300 mM) was suspended in the nonionic surfactant Pluronic F-68 (12 mM) as described previously (Katz et al., *Proc. Natl. Acad. Sci. U.S.A.*, 88:10825–10829, 1991, hereby incorporated by reference). A vehicle control was prepared using the same procedure except n-docosanol was omitted. Keloid cells ($2.7 \times 10^4$ per well) were added to 16 mm wells containing DMEM supplemented with 10% fetal calf serum (FCS), sodium pyruvate, L-glutamine and penicillin/streptomycin. n-Docosanol (15 mM) or the corresponding Pluronic F-68 control (0.6 mM) was added (total volume=2.0 ml). Cells were harvested after incubation for 72 and 168 hours at 37° C. in a humidified 10% $CO_2$ incubator. The number of viable cells was determined by trypan blue staining. The results are shown in Table 1.

TABLE 1

| Condition | 72 hours | | 168 hours | |
| --- | --- | --- | --- | --- |
| | cells/well | % control* | cells/well | % control* |
| no addition | $3.2 \times 10^4$ | 100 | $4.2 \times 10^4$ | 100 |
| control suspension | $2.9 \times 10^4$ | 91 | $2.9 \times 10^4$ | 69 |
| 15 mM n-docosanol | $3.3 \times 10^4$ | 103 | $1.0 \times 10^4$ | 24 |

*Compared to cells incubated with no addition

In view of the initial cell inoculum, the cell number after a 72 hour incubation indicates that cultured keloids are slow-growing relative to other cell types. After 168 hours, cells without addition were at 1.5× the initial cell density. The growth of n-docosanol-treated cells was inhibited 76% compared to no addition, while control (Pluronic F-68 treated) cell growth was only inhibited 31% compared to no addition. Thus, n-docosanol treatment resulted in a dramatic inhibition of keloid cell growth in vitro.

The experiment described in Example 1 was repeated. However, human fetal lung cells were also subjected to the same treatments as the keloid fibroblasts and growth results were compared.

EXAMPLE 2

Comparison of N-docosanol Effect Between Keloid and Normal Cells

Human fetal lung cells (HFL; ATCC CCL 153) and keloid cells ($5 \times 10^4$ cells/well) were separately added to 16 mm wells and treated as described in Example 1. The results are shown in Tables 2 (keloid cells) and 3 (human fetal lung cells).

TABLE 2

| Condition | 72 hours | | 168 hours | |
| --- | --- | --- | --- | --- |
| | cells/well | % control* | cells/well | % control* |
| no addition | $1.7 \times 10^4$ | 100 | $2.7 \times 10^4$ | 100 |
| control suspension | $1.2 \times 10^4$ | 71 | $2.1 \times 10^4$ | 78 |
| 15 mM n-docosanol | $1.1 \times 10^4$ | 64 | $0.4 \times 10^4$ | 15 |

*Compared to cells incubated with no addition

TABLE 3

| Condition | 72 hours | | 168 hours | |
| --- | --- | --- | --- | --- |
| | cells/well | % control* | cells/well | % control* |
| no addition | $5.0 \times 10^4$ | 100 | $8.0 \times 10^4$ | 100 |
| control suspension | $4.2 \times 10^4$ | 84 | $2.3 \times 10^4$ | 30 |
| 15 mM n-docosanol | $5.8 \times 10^4$ | 116 | $20 \times 10^4$ | 250 |

*Compared to cells incubated with no addition

As shown in Table 2, n-docosanol inhibited the number of keloid cells per well by 36% at 72 hours and by 85% at 168 hours. The vehicle control inhibited 29% at 72 hours and 22% at 168 hours. In contrast, at both time intervals the number of human fetal lung cells was significantly increased in the n-docosanol treated group, while the control suspension inhibited lung cell growth by 70%. These results show that the inhibition of cell proliferation mediated by n-docosanol is not a generalized phenomena, but is specific for hyperproliferative cells.

The following experiment examined the effect of n-docosanol on cell proliferation and quantitation of n-[1-$^{14}$C]docosanol binding to keloid, Vero (normal African green monkey kidney; ATCC CCL 81) and normal skin fibroblast (ATCC CRL 1900) cells.

EXAMPLE 3

N-docosanol Binding and Proliferation Studies

Human keloid fibroblasts, normal control skin fibroblasts and Vero cells were obtained from ATCC. n-Docosanol (30 mM) was suspended in Pluronic F-68 (1.2 mM) as described previously (Katz et al., ibid). A vehicle control was prepared using the same procedure except for the omission of n-docosanol. Radiolabeled n-[1-$^{14}$C] docosanol suspension was prepared as described by Katz et al. (ibid.). Cells were resuspended in $1.2 \times 10^6$ cells/ml in DMEM supplemented with 10% fetal calf serum, sodium pyruvate, L-glutamine and penicillin-streptomycin. Cell suspension (0.5 ml) was added to each 35 mm well containing 1.3 ml media, followed by addition of 0.2 ml radiolabeled n-docosanol suspension (final n-docosanol concentration=3 mM). After 24 hours at 37° C. in humidified 10% $CO_2$, the suspension was removed, wells were washed extensively with saline and cells were solubilized for scintillation counting by incubation with 0.5 ml trypsin for 15 min at 37° C. Solubilized cells were counted in a Beckman LS6000 scintillation counter. Samples were corrected for nonspecific binding to plates by subtracting values obtained in control wells lacking cells. To determine cell number, duplicate plates were treated with non-radiolabeled n-docosanol or control suspension at the same concentration or were left untreated. The number of viable cells was determined by trypan blue staining. The results are summarized in Table 4.

TABLE 4

| Addition | Keloid No. cells | % ctrl | CRL-1900 No. cells | % ctrl | Vero No. Cells | % ctrl |
|---|---|---|---|---|---|---|
| none | $3.7 \times 10^5$ | 100 | $5.5 \times 10^5$ | 100 | $3.9 \times 10^5$ | 100 |
| control | $2.3 \times 10^5$ | 62 | $5.2 \times 10^5$ | 95 | $5.1 \times 10^5$ | 131 |
| n-docosanol (3 mM) | $1.6 \times 10^5$ | 43 | $5.4 \times 10^5$ | 98 | $5.9 \times 10^5$ | 151 |
| Binding per $10^6$ cells | 45.5 µg | | 15.6 µg | | 8.9 µg | |

*Compared to cells incubated with no addition

As shown in Table 4, n-docosanol reduced the number of keloid cells by 57% after a one day incubation, while the control suspension reduced the number of keloid cells by 38%. Conversely, the numbers of CRL-1900 normal skin fibroblasts and Vero cells were not decreased in the presence of n-docosanol. About three fold greater amounts of radiolabeled n-docosanol bound to keloid as compared to CRL 1900 or Vero cells. The increased binding and subsequent uptake of n-docosanol in keloid cells illustrates the selective toxicity of the compound to hyperproliferative cell types.

The case report described below illustrates the clinical use of n-docosanol (LIDAKOL™) in treatment of keloid scar formation.

EXAMPLE 4

Treatment of Keloid Scar Formation with N-docosanol

L. L., a 34 year old black male, presented with a one year history of progressive bilateral facial keloid scarring. The precise cause of injury is unknown, but appears to have been initiated as a result of work-related exposure to some aerosolized irritant at a high rise building construction site. During the time of exposure, the patient was working in an area in which noxious fumes were known to exist, and he was wearing a filtration face mask for protection against inhalation exposure. Since the resulting wounds occurred in a pattern which appeared to outline the edges of the protective face mask, the injury may reflect some type of chemical burn resulting from concentration of aerosolized irritants with perspiration at the edge of the face mask. The injuries first appeared as ulcerating wounds at the temple mark on each side of the face and extended progressively downward along the mandibular lines, usually erupting as ulcerated sores which, as they healed, resulted in keloid scarring at the affected sites.

During the ensuing year after onset of this process, the patient was seen on several occasions in the dermatology division of a major local hospital and attempts were made to arrest the process by intradermal steroid injections at the affected sites. This treatment approach was ineffective. When the patient was first seen by the inventors, he had extensive and disfiguring bilateral scars on the face and a large ulcerated lesion at the lower end of the process on the right side of the face. There was keloid scarring on both the right and left sides of the face manifested as typical "ropey and cord-like" tissue deposition and depigmentation. The right side of the face was noticeably swollen presumably as a result of the active ulceration process at the lower end of the lesions. The patient complained of pain along both areas of scarring, particularly at the more distal ends of the lesions. He admitted to social withdrawal as a result of embarrassment about his appearance and extreme frustration about the apparent futility of obtaining any help to arrest or reverse the process.

After thoroughly explaining the experimental aspects of the therapeutic regimen, the patient volunteered to enter a study in which cream containing either 15% or 10% n-docosanol as active ingredient was to be applied to the affected areas. These topical cream formulations are described in U.S. Pat. No. 5,534,554, the entire contents of which are incorporated by reference. Initially, applications of cream containing 15% n-docosanol were made three times daily. This cream formulation contained, in addition to 15% n-docosanol, 11.0% sucrose stearates, 5.0% sucrose cocoate, 8.0% mineral oil NF, 5.0% propylene glycol USP, 2-ethyl-1,3-hexanediol and 58.3% purified water (all weight percent). After one month on this regimen, the patient was changed to cream containing 10% n-docosanol and the application frequency was reduced to two times daily, after showering in the morning and just before bed in the evening. This cream composition contained, in addition to 10% n-docosanol, 5.0% sucrose stearates, 8.0% mineral oil NF, 5.0% propylene glycol USP, 2.7% benzyl alcohol NF and 69.3% purified water.

Almost immediately after onset of therapy, the patient reported a significant diminution in pain around the lesions, and within 48 hours the inventors observed a significant reduction in swelling on the right side of the face and onset of granulation within the ulcerated lesion at the distal end of the affected area in the right side of the face. By the end of the second week of therapy, the patient could perceive a diminution in tightness and thickness of the keloids and a greater suppleness of the overlying dermis.

After three months of therapy there was a clear reduction in the extent of elevation of the keloid scarring and a considerable improvement in skin pigmentation. At the site of the healed ulcerated lesion on the right side of the face, the resulting wound repair left a much smaller scar defect compared to the large scarred area at the right temple line which was the site of healing of the initial ulcer at the onset of this process. After one year of therapy, there was a significant reduction of scar tissue, a flattening of the previously ropey and cord-like elevations and almost complete return to normal pigmentation in the affected areas. The patient exhibited no adverse reactions during the course of treatment.

EXAMPLE 5

The treatment described in Example 4 is repeated with other C18 to C26 aliphatic alcohols. The active compounds are used in the therapeutic regimen described in Example 4 in a patient with excessive keloid formation, substituting the appropriate alcohol for n-docosanol. Similar improvements in the condition are observed.

EXAMPLE 6

Treatment of Kaposi's Sarcoma

HIV-positive male patients presenting with treatment-resistant cutaneous Kaposi's sarcoma were treated for 28 days, 5 times daily with the 10% n-docosanol cream formulation described in Example 4. Response to treatment was evaluated according to lesion dimensions, color of the lesion and the type of lesion (hard, soft or nodule). The data were recorded on intermittent days throughout the 28 days of the study and values were compared to baseline observations made on Day 1. Three target lesions were evaluated in each patient. Thus far, five patients have completed the study.

Data on lesion size and color for Day 1 (baseline) and Day 28 are indicated in Table 5. In three out of five patients a response to the treatment was indicated by a reduction in the size of the lesions at Day 28 compared to the baseline measurements of Day 1. A reduction in lesion size was observed in 2 out of 3 lesions in one patient and in 3 out of 3 lesions in two patients. One lesion completely disappeared by Day 3. An increase in lesion size was not observed for any of the 15 lesions studied. In all five patients, color changes in all lesions to a lighter color suggested that treatment caused a decrease in lesion severity. One patient who reported painful lesions on Day 1 reported that the lesions were less painful on Day 15 and thereafter, and this was accompanied by a decrease in the clinically observed swelling.

TABLE 5

| Patient | Lesion Number | Day 1 Diameter (mm) | Day 1 Color | Day 28 Diameter (mm) | Day 28 Color | percent reduction in lesion size |
|---|---|---|---|---|---|---|
| WEB | 1 | 100 | purple | 25 | pale | 75 |
| WBB | 2 | 54 | deep pink | gone | gone | gone |
| WEB | 3 | 380 | purple | 100 | pale pink | 74 |
| DMS | 2 | 400 | purple | 324 | very pale pink | 19 |
| DMS | 3 | 500 | purple | 360 | pale pink | 20 |
| DMS | 4 | 100 | purple | 100 | pale pink | 0 |
| CKW | 1 | 170 | deep burgundy | 170 | pink | 0 |
| CKW | 4 | 289 | deep burgundy | 289 | pink | 0 |
| CKW | 7 | 121 | deep burgundy | 121 | pink | 0 |
| SHC | 6 | 198 | purple | 160 | tan | 19 |
| SHC | 7 | 500 | purple | 360 | tan | 28 |
| SHC | 8 | 1200 | purple | 1080 | tan | 10 |
| TLM | 5 | 9 | pink | 9 | lighter pink | 0 |
| TLM | 6 | 250 | pink | 250 | lighter pink | 0 |
| TLM | 7 | 360 | pink | 360 | lighter pink | 0 |

*Target lesion dimensions represent the product of two measured perpendicular diameters.

EXAMPLE 7

The treatment described in Example 6 is repeated with other C18 to C26 aliphatic alcohols. The active compounds are used in the therapeutic regimen described in Example 6 in patients with Kaposi's sarcoma, substituting the appropriate alcohol for n-docosanol. Similar improvements in the condition are observed.

It should be noted that the present invention is not limited to only those embodiments described in the Detailed Description. Any embodiment which retains the spirit of the present invention should be considered to be within its scope. However, the invention is only limited by the scope of the following claims.

What is claimed is:

1. A method of treating or inhibiting the growth of a hyperproliferative skin lesion in an individual in need thereof, comprising topically administering to said lesion an effective proliferation-inhibiting amount of one or more C18 to C20 aliphatic alcohols in a pharmaceutically acceptable carrier.

2. The method of claim 1, wherein said skin lesion is benign.

3. The method of claim 2, wherein said skin lesion is keloid.

4. The method of claim 1, wherein said skin lesion is malignant.

5. The method of claim 1, wherein said skin lesion is Kaposi's sarcoma or skin cancer.

6. The method of claim 1, wherein said C18 to C20 aliphatic alcohol is present in an amount from about 0.1% to 20% by weight.

7. The method of claim 1, wherein said C18 to C20 aliphatic alcohol is present in an amount from about 5% to 15% by weight.

* * * * *